(12) United States Patent
Evans et al.

(10) Patent No.: US 7,722,622 B2
(45) Date of Patent: May 25, 2010

(54) IMPLANT INSERTION APPARATUS AND METHOD OF USE

(75) Inventors: David E. Evans, Downingtown, PA (US); Douglas S. Kephart, Glen Mills, PA (US)

(73) Assignee: Synthes USA, LLC, West Chester, PA (US)

( * ) Notice: Subject to any disclaimer, the term of this patent is extended or adjusted under 35 U.S.C. 154(b) by 1063 days.

(21) Appl. No.: 11/354,986

(22) Filed: Feb. 16, 2006

(65) Prior Publication Data

US 2006/0195097 A1 Aug. 31, 2006

(51) Int. Cl.
*A61B 17/60* (2006.01)
*A61F 2/44* (2006.01)

(52) U.S. Cl. .................................... 606/99; 606/86 A (58) Field of Classification Search ............... 606/86 A, 606/914, 99
See application file for complete search history.

(56) References Cited

U.S. PATENT DOCUMENTS

| | | | | |
|---|---|---|---|---|
| 3,353,718 A | * | 11/1967 | Mclay | 222/158 |
| 3,486,505 A | * | 12/1969 | Morrison | 606/90 |
| 4,832,692 A | * | 5/1989 | Box et al. | 604/99.01 |
| 5,306,248 A | * | 4/1994 | Barrington | 604/97.02 |
| 5,431,658 A | | 7/1995 | Moskovich | 606/99 |
| 5,797,909 A | | 8/1998 | Michelson | 606/61 |
| 6,048,336 A | * | 4/2000 | Gabriel | 604/211 |
| 6,096,038 A | | 8/2000 | Michelson | 606/61 |
| 6,159,215 A | | 12/2000 | Urbahns et al. | 606/86 |
| 6,440,142 B1 | | 8/2002 | Ralph et al. | 606/99 |
| 6,478,800 B1 | | 11/2002 | Fraser et al. | 606/99 |
| 6,663,638 B2 | | 12/2003 | Ralph et al. | 606/99 |
| 6,755,841 B2 | * | 6/2004 | Fraser et al. | 606/99 |
| 6,916,308 B2 | * | 7/2005 | Dixon et al. | 604/122 |
| 2002/0013553 A1 | | 1/2002 | Pajunk et al. | |
| 2002/0072752 A1 | | 6/2002 | Zucherman et al. | 606/99 |
| 2003/0109884 A1 | | 6/2003 | Tague et al. | |
| 2005/0027300 A1 | | 2/2005 | Hawkins et al. | 606/86 |
| 2005/0165408 A1 | * | 7/2005 | Puno et al. | 606/99 |
| 2006/0293692 A1 | * | 12/2006 | Whipple et al. | 606/104 |
| 2007/0185375 A1 | * | 8/2007 | Stad et al. | 600/101 |

OTHER PUBLICATIONS

International Preliminary Examination Report on Patentability dated Aug. 28, 2007.

* cited by examiner

*Primary Examiner*—Eduardo C Robert
*Assistant Examiner*—Ellen C Hammond
(74) *Attorney, Agent, or Firm*—Stroock & Stroock & Lavan LLP

(57) ABSTRACT

An apparatus for use with a spinal implant includes a handle structure with a passage. A shaft with a screw thread that is moveable within the passage in the handle structure. A pusher block is linked to the shaft, and has a forward surface configured to engage the spinal implant. A screw-threaded clutch member is supported on the handle structure for movement into and out of engagement with the screw thread on the shaft.

26 Claims, 6 Drawing Sheets

IMPLANT INSERTION APPARATUS AND METHOD OF USE

CROSS REFERENCE TO RELATED APPLICATION

The present application claims priority to U.S. Provisional Application No. 60/656,707 filed Feb. 25, 2005, the entire content of which is expressly incorporated herein by reference thereto.

TECHNICAL FIELD

This technology relates to devices that are used to install implants, for example, in the human spine.

BACKGROUND

A spinal implant inserter is a device that installs an implant between two (e.g., a pair of adjacent) vertebrae, or wholly or partially within a vertebra, in the human spine. Such a device is typically operated manually, and may include a rod that the operator uses to push the spinal implant into the intravertebral space. The inserter may be used, for example, for an anterior approach, a posterior approach, a lateral approach, or any variation in between.

SUMMARY

An apparatus for use with a spinal implant which may comprise a handle structure which may have a longitudinal axis and a passage, a shaft which may be movable within the passage and may have at least a portion having a first screw thread, a pusher block which may be operably connected to the shaft and may have a forward surface configured to engage the spinal implant, and a clutch member which may be supported on the handle structure for movement into and out of engagement with the first screw thread of the shaft. The apparatus may also include a pair of paddles which may have a distal end, a proximal end and may project from the handle. The inserter may be used, for example, for an anterior approach, a posterior approach, a lateral approach, or any variation in between.

The handle structure may have an internal thread, and the shaft may have a second screw thread movable along the longitudinal axis into engagement with the internal thread on the handle structure when the clutch member is either engaged or disengaged with the first screw thread of the shaft. In some embodiments, the handle may have an internal thread and the shaft may have at least a portion which may have a first screw thread spaced from the internal thread such that the shaft can slide axially through a first range of movement in the passage. At least a different portion of the shaft may have a second screw thread. The second screw thread may be moveable into engagement with the internal thread such that the shaft can only be rotated through a second range of movement in the passage. The shaft may be configured for the second range of movement to follow the first range of movement when the shaft is moved forward through the passage.

The pusher block may be moveable with and linked to the shaft. The pusher block may have a receiving portion sized and configured to receive an ejector rod. The ejector rod may comprise a central portion having a longitudinal axis and two arms extending from the central portion. In one embodiment, the arms may be offset from the longitudinal axis of the central portion. The central portion of the ejector rod may comprises a plurality of indentations and a groove. The pusher block may have at least one fastener for engaging the indentations and groove such that the ejector rod may be rotatable relative to the pusher block. In some embodiments, the ejector rod may have at least one arm and may be operably connected to and/or disengageable from the pusher block. In an embodiment where at least one paddle has a slot, the at least one arm may be moveable in the slot between the distal and proximal ends of the paddle. The ejector rod may be releasably connected to the pusher block. At least one of the paddles may comprise an opening such that when the ejector rod is positioned in the opening, the ejector rod may be disengageable from and/or rotatable relative to the pusher block.

At least a portion of the shaft may be located between the paddles and may move through the proximal end of the paddles. The distal ends of the paddles may be sized and configured to be positioned between adjacent vertebrae. Moreover, the paddles may be configured so that the distal ends of the paddles are biased together. The proximal end of the paddles may be sized and configured to be operably attached to the handle. In one embodiment, at least one paddle may have at least one ridge at the distal end thereof, the ridge may enhance engagement of the at least one paddle with a vertebrae. In some embodiments, at least one paddle may have at least one stop structure for engaging at least one vertebrae, the at least one stop structure may be configured to prevent over penetration of the distal end of the paddles into adjacent vertebrae. At least one of the pair of paddles may have a slot such that the ejector rod may move along the slot. The paddles may be configured so that the distal ends of the paddles may move away from each other as the pusher block moves from the proximal end of the paddles to the distal end of the paddles.

The clutch member may comprise an opening therethrough having a first portion and a second portion, wherein the first portion may comprise a threaded portion and the second portion may comprise an unthreaded portion. The clutch member may also comprise a first side portion and at least a pair of pockets on the side portion. The handle may have a first fastener which may selectively engage only one of the pair of pockets at a time. The clutch member may further comprise a second side portion and a second pair of pockets on the second side portion. The handle may have a second fastener which may selectively engage only one of the second pair of pockets at a time. In one embodiment, the first and second fasteners may be ball detents positioned through the handle. The clutch member may be supported on the handle for movement into and out of engagement with the first screw thread on the shaft such that the shaft may only rotate through a first range of movement in the passage when the clutch member is engaged with the first screw thread. The clutch member may be supported on the handle structure for movement between a first position, wherein the shaft is capable of sliding within the handle parallel to the longitudinal axis, and a second position, wherein the shaft is capable of moving within the handle in a second manner different than longitudinal movement. The second different manner of movement may include at least in part by rotating the shaft.

A method of inserting an implant between adjacent vertebrae may comprise providing an implant inserter comprising a handle structure which may have a longitudinal axis and a passage, a pair of paddles which may extend from the handle and may have a distal end and a proximal end, a shaft which may be moveable within the passage and at least a portion which may have a first threaded portion, a pusher block which may be operably connected to the shaft and may have a forward surface which may be configured to engage the spinal implant, and a clutch member, at least a portion of which may have screw threads for selectively engaging the first threaded portion of the shaft. The method may further comprise inserting an implant against the pusher block and in between the paddles, inserting the distal ends of the paddles in between adjacent vertebrae, moving the shaft through the passage of the handle such that the implant may move towards the distal end of the paddles and may spread the paddles apart, and withdrawing the paddles from in between adjacent vertebrae. Additionally, the method may include moving the screw threads of the clutch member into engagement with the first threaded portion of the shaft. Moreover, in an embodiment wherein the shaft may comprise a second threaded portion and the handle may comprise an internal thread, the method may further comprise engaging the second threaded portion of the shaft with the internal thread of the handle and rotating the shaft relative to the handle to move the pusher block between the paddles. The paddles may be moved apart as the implant moves towards the distal ends of the paddles. In embodiments where the implant inserter may comprise an ejector rod operably connected to the pusher block, the ejector rod may be engaged with at least one vertebrae such that as the shaft rotates the distal ends of the paddles may move out from in between adjacent vertebrae. Furthermore, in an embodiment where the implant inserter may comprise an ejector rod operably connected to the pusher block and at least one of the paddles may comprise an opening, the method may further comprise rotating the ejector rod within the opening.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

DETAILED DESCRIPTION

The apparatus 10 shown in the drawings is a spinal implant inserter with parts that are examples of the structural elements recited in the claims. The inserter 10 thus includes examples of how a person of ordinary skill in the art can make and use the invention, and is described here to provide enablement and best mode of the invention without imposing limitations that are not recited in the claims. The drawings thus are illustrative of the inserter and are for purposes of description. In this regard, while the apparatus is described and illustrated for purposes of inserting an implant into the spine, it may be used for other types of implants to be inserted in other locations and in animals/objects other than humans.

Figure 1:
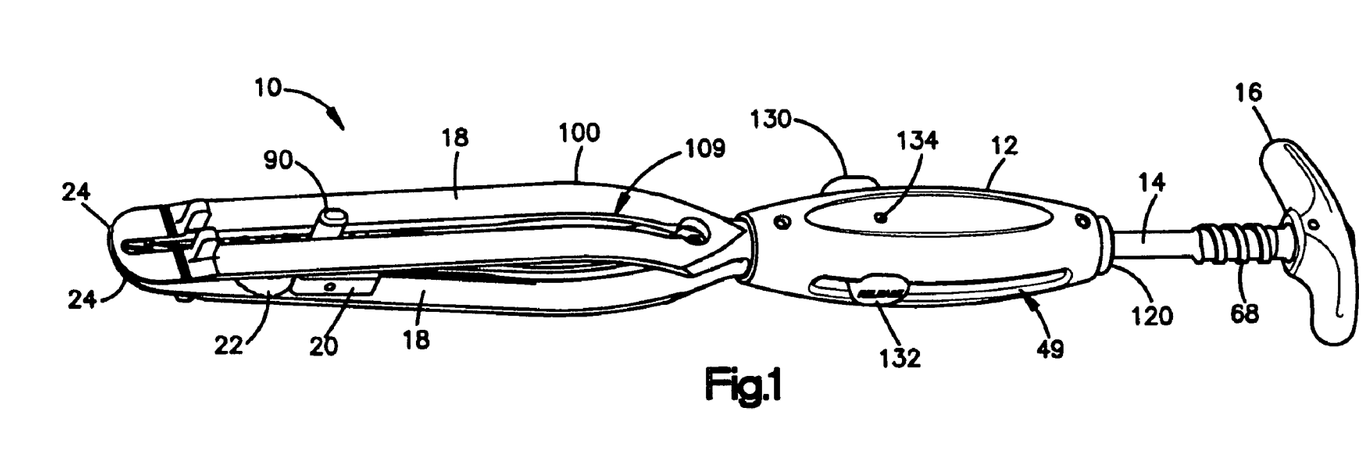
FIG. 1 is a perspective view of a spinal implant inserter with a spinal implant.

The parts of the inserter 10 that are shown in FIG. 1 include a grip handle 12, a shaft 14, and a T-handle 16 on the end of the shaft 14. A pair of distracter springs 18, which may be referred to as paddles, may project forward from the grip handle 12. The shaft 14 may extend through the grip handle 12, and may project forward from the grip handle 12 between the paddles 18.

A pusher block 20 may be received between the paddles 18. The pusher block 20 may be linked to or associated with the shaft 14 to be driven forward as the operator moves the T-handle 16 forward toward the grip handle 12. The pusher block 20 may then push a spinal implant 22 forward between the distal ends 24 of the paddles 18, which forces the paddles 18 apart from each other to simultaneously distract a pair of vertebrae and advance the implant 22 into the intravertebral space.

Figure 2:
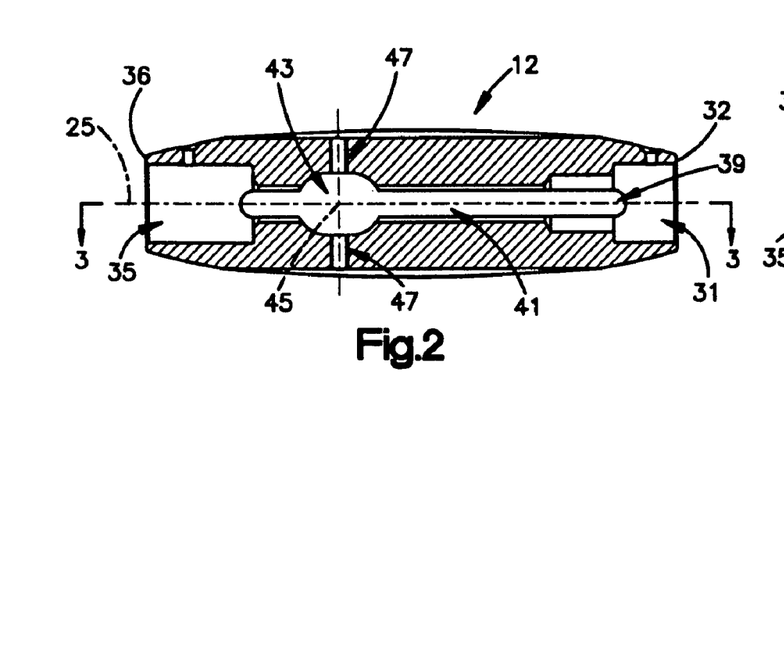
FIG. 2 is a sectional view of a part of the inserter shown in FIG. 1.
Figure 3:
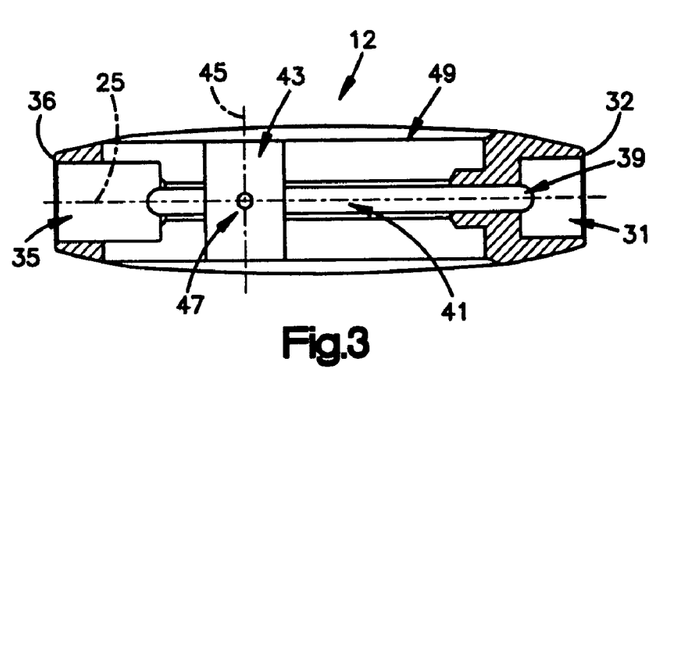
FIG. 3 is a sectional view taken on line 3-3 of FIG. 2.

As shown separately in FIGS. 2 and 3, the grip handle 12 may have a generally cylindrical configuration with a longitudinal central axis 25, and may be tapered radially inward toward its opposite ends. A counterbore 31 may extend axially inward from the proximal end 32 of the grip handle 12, which is on the right as viewed in the drawings. A similar counterbore 35 may extend axially inward from the distal end 36, which is on the left as viewed in the drawings. The counterbores 31, 35 and an inner bore 39 together may define a passage 41 extending longitudinally through the grip handle 12 along the axis 25. In one embodiment, the handle 12 may be about 10 cm to about 15 cm in length.

Another passage 43 may extend transversely through the grip handle 12. That passage 43 may cross the longitudinal passage 41, and may be centered on a transverse axis 45 perpendicular to the longitudinal axis 25. A pair of narrow, screw-threaded bores 47 may extend oppositely outward from the transverse passage 43, as best shown in FIG. 2. Also extending transversely through the grip handle 12 may be a slot 49 which, as best shown in FIG. 1, may be elongated lengthwise of the grip handle 12.

Figures 4, 5:
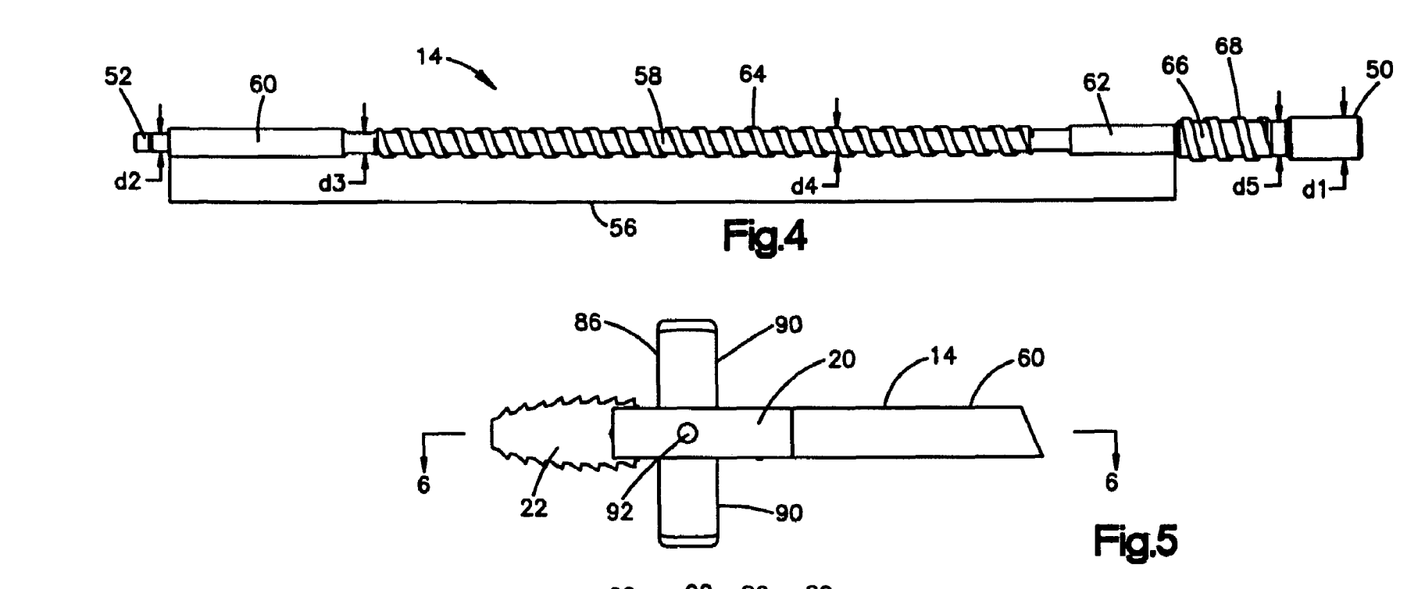
FIG. 4 is a side view of a part of the inserter of FIG. 1.
FIG. 5 is an enlarged view of the implant and parts of the inserter of FIG. 1.

The shaft 14 may have several distinct sections with differing lengths and diameters. As shown in FIG. 4, these may include a proximal end section 50 with the largest diameter d1 on the shaft 14, and a distal end section 52 with the smallest diameter d2. The proximal end section 50 may be configured to receive the T-handle 16 (FIG. 1). The distal end section 52 may be configured to receive the pusher block 20 (FIG. 1). In one embodiment, the shaft 14 may be about 30 cm to about 40 cm in length. In a one embodiment, the inserter 10 may be about 35 cm to about 45 cm in length.

Other sections of the shaft 14 may include a major length section 56 which, in turn, may include a middle section 58 between two intermediate sections 60 and 62. The middle section 58 may be the longest individual section of the shaft 14, and may have a first screw thread 64 extending along nearly its entire length. The middle section 58 may have a third diameter d3 beside the screw thread 64, and may have a fourth diameter d4 at the screw thread 64. The intermediate sections 60 and 62 also may have the fourth diameter d4. Another intermediate section 66 with a larger diameter d5 may extend axially between the proximal end section 50 and the adjacent unthreaded intermediate section 62. That section 66 of the shaft 14 may have a second screw thread 68 with the largest diameter d1.

Figure 6:
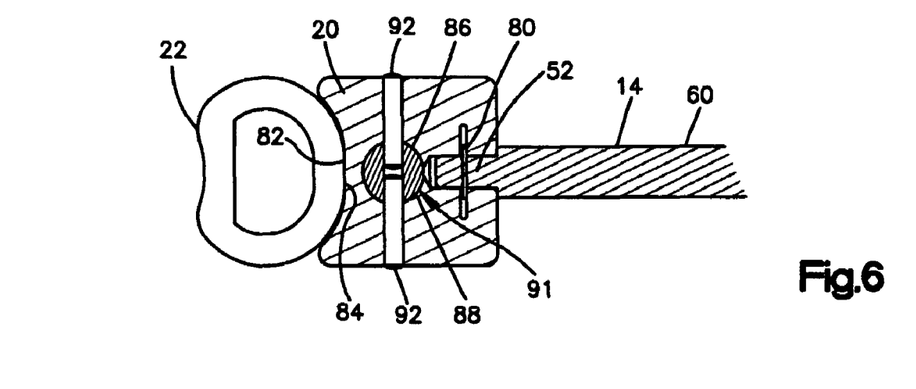
FIG. 6 is a sectional view taken on line 6-6 of FIG. 5.
Figure 7:
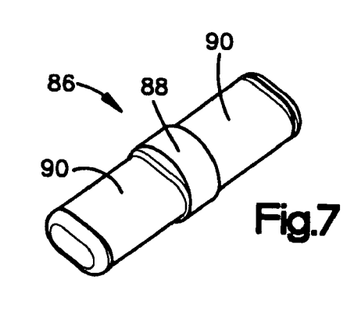
FIG. 7 is a perspective view of a part shown in FIGS. 5 and 6.

As shown in enlarged detail in FIGS. 5 and 6, the pusher block 20 may be mounted on the distal end section 52 of the shaft 14, and may be retained on the shaft 14 by a retainer ring 80. A forward surface 82 of the pusher block 20 may have a contour matching the contour of an opposed surface 84 of the spinal implant 22. Also shown in FIGS. 5 and 6 is an ejector rod 86 that may be mounted on the pusher block 20. As shown separately in FIG. 7, the ejector rod 86 may have a central portion 88 with a circular cross-section, and may have a pair of arms 90, which may have oval, elliptical, or any other suitable cross-sections. It should be noted that the ejector rod 86 may have at least one arm 90. The central portion 88 of the ejector rod 86 may be received in a circular bore 91 extending through the pusher block 20, as shown in FIG. 6. The arms 90 may project from the pusher block 20, as shown in FIG. 5. A pair of fasteners 92 may secure the ejector rod 86 on the pusher block 20.

Figure 8:
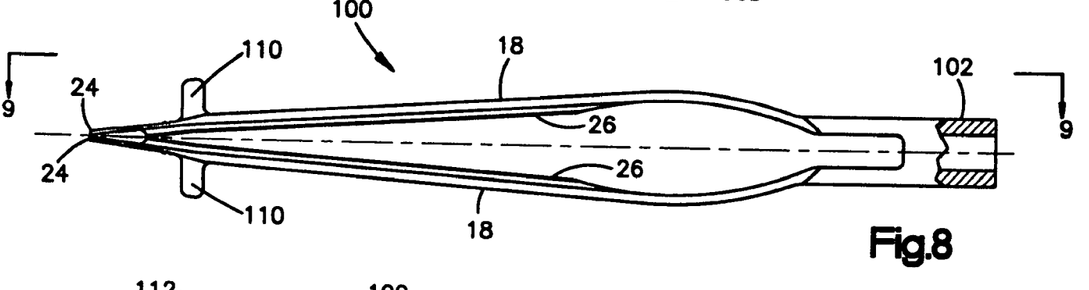
FIG. 8 is a side view of a part of the inserter of FIG. 1.
Figure 9:
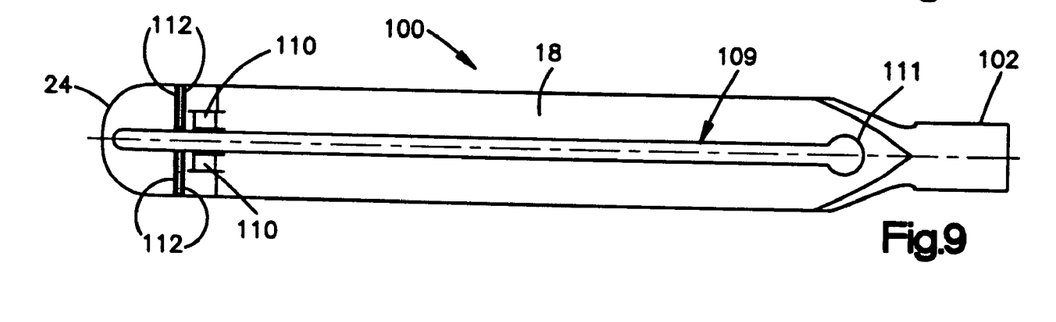
FIG. 9 is a top view of the part shown in FIG. 8.

There may be one paddle 18 or a plurality of paddles 18. In the illustrated embodiment, the inserter 10 has two paddles 18. The paddles 18 may be, as illustrated, separately flexible portions of a unitary spring structure 100, or in another embodiment, may be an assembly of multiple (e.g., two) springs affixed to a base. As shown in FIGS. 8 and 9, the spring structure 100 may have a tubular base 102 at its proximal end. The paddles 18 may be alike, and may be configured as elongated leaf springs that bow transversely outward from the base 102 and converge at their distal ends 24. At least one paddle 18 may have a centrally located slot 109 with a keyhole shaped opening 111 near the base 102. The opening 111 may provide a means by which the ejector rod 86 may be separated from the pusher block 20 so that a replacement ejector rod or ejector rod having a different configuration may be used with the inserter 10. For example, when the ejector rod 86 is positioned proximate or within the opening 111, the fasteners 92 may be disengaged from the ejector rod 86 and the ejector rod 86 may be removed from the pusher block 20 and removed from the opening 111.

Figure 7A:
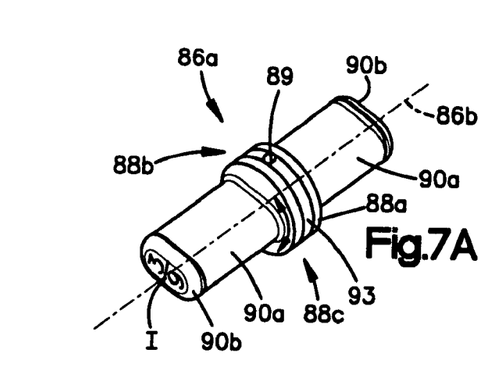
FIG. 7A is a perspective view of an alternative embodiment of the part of FIG. 7.

As shown in FIG. 7A, an alternative ejector rod 86*a* may be used with the inserter 10. The ejector rod 86*a* may have arms 90*a* and a central portion 88*a* having a longitudinal axis 86*b*. It should be noted that the ejector rod 86*a* may have at least one arm 90*a*. The arms 90*a* may be off-center with respect to the longitudinal axis 86*b* of the central portion 88*a*. Moreover, the ejector rod 86*a* may have one or more indentations 89 and a groove 93. The ejector rod 86*a* may be held in the pusher block 20 by fasteners 92 such as, for example, ball detents (not shown) which may engage the indentations 89. When the arms 90*a* are located within the opening 111 of the paddles 18, the central portion 88*a* may be rotated within the opening 111. A surgeon may rotate the ejector rod 86*a* such that the fasteners 92 may be disengaged from the indentations 89 and move along the groove 93. The fasteners 92 may then be engaged with another indentation 89 so that the arms 90*a* are closer or farther away from the distal ends 24 of the paddles 18. Such a construction may enable a surgeon to control the countersink depth of the implant 22 between the vertebrae. For example, in a position where a first side 88*b* of the central portion 88*a* faces the distal ends 24, the countersink depth of the implant 22 may be about 3 mm, and in a position where a second side 88*c* of the central portion 88*a* faces the distal ends 24, the countersink depth of the implant 22 may be about 6 mm. The arms 90*a* may have surfaces 90*b* with indicia I which provide a visual indication of the countersink depth of the implant 22 when the ejector rod 86*a* is in different orientation.

A pair of stop structures 110 may project from opposite sides of the slot 109 near the distal end 24 of the paddle 18. The stop structures 110 prevent the inserter 10 from advancing too far into the intravertebral space. As further option, the stop feature may be adjustable to pre-select the desired insertion distance. For example, there may be two insertion distance options effected by a stud or nub which may be hingedly attached to the stop structures 110 for positioning either distal to, or proximal to, the stop structures 110, at the election of the instrument user.

Each paddle 18 further may have a pair of parallel, narrow ridges 112 that are closely spaced apart from each other at locations forward of the stop structures 110. The narrow ridges 112 may act as a retention feature to prevent the inserter 10 from dislodging itself while in operation. Each pair of ridges 112 may be interrupted by the adjacent slot 109, but may otherwise extend fully across the respective paddle 18. In a one embodiment, the paddles 18 may be about 17 cm to about 27 cm in length.

Figure 10:
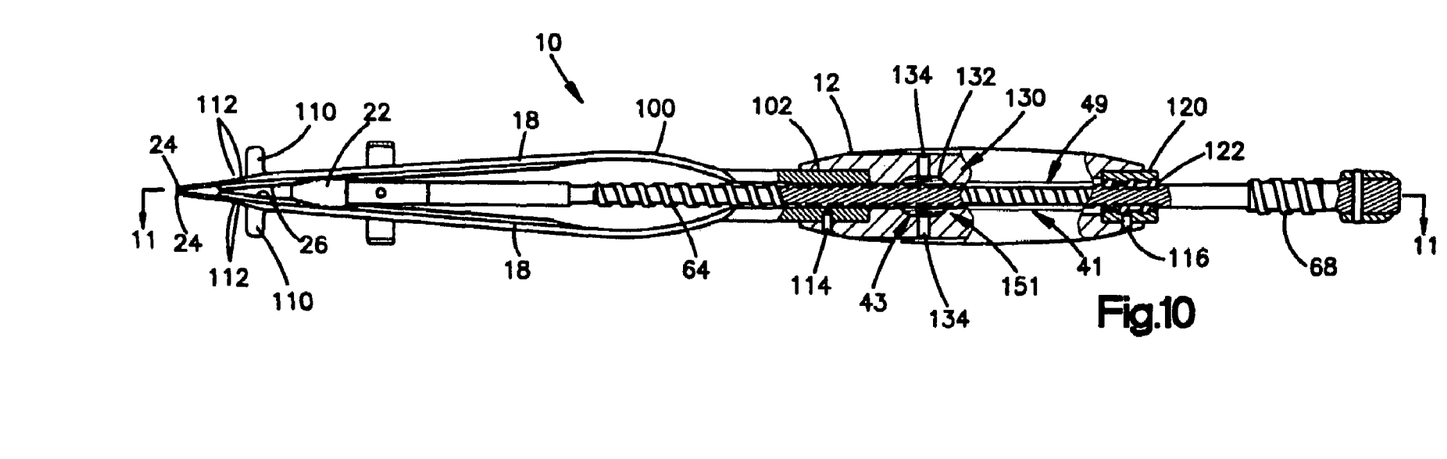
FIG. 10 is a side view of the implant and inserter of FIG. 1, with certain parts shown in section.
Figure 11:
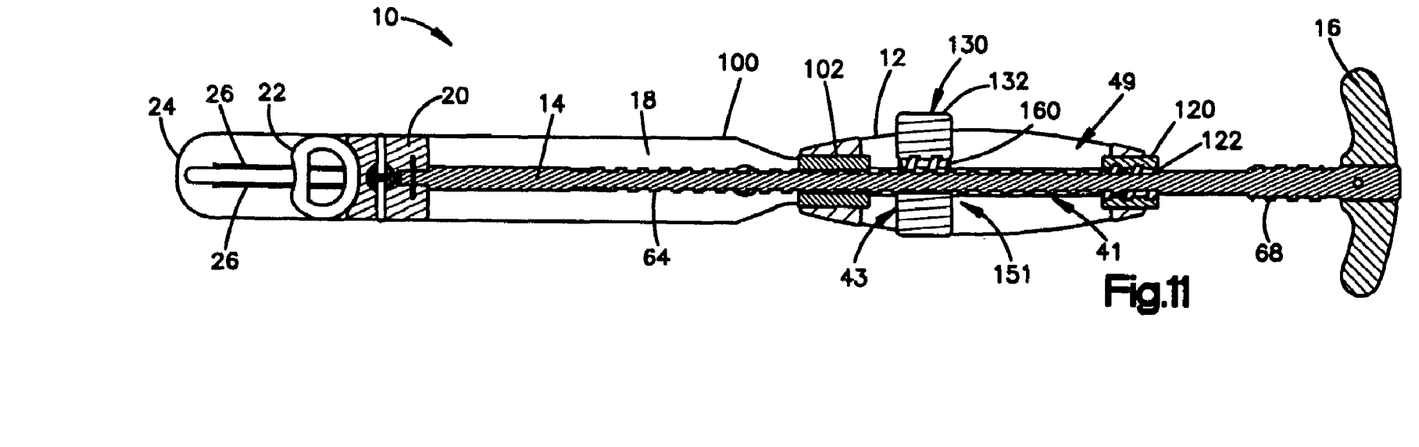
FIG. 11 is a view taken on line 11-11 of FIG. 10.
Figure 12:
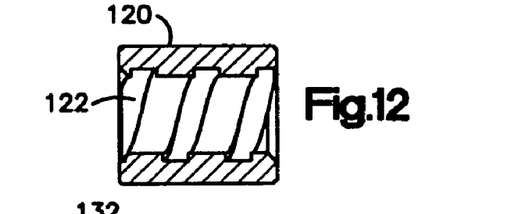
FIG. 12 is a sectional view of a part of the inserter of FIG. 1.
Figure 13:
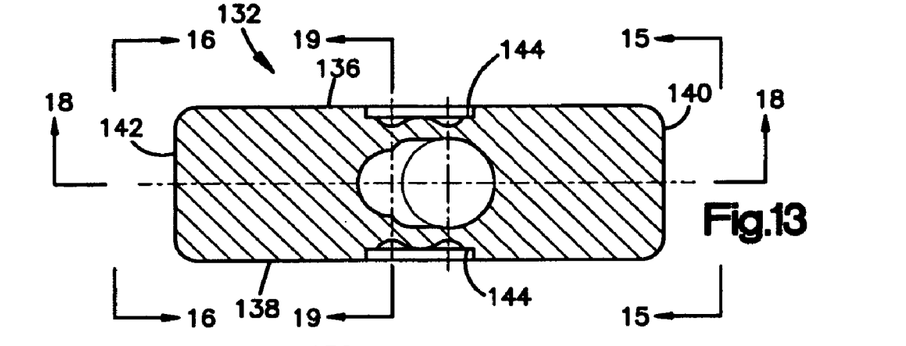
FIG. 13 is a side view, taken in section, of a part of the inserter of FIG. 1.

As shown in FIGS. 10 and 11, the base 102 of the spring structure 100 may be received in the distal counterbore 35 in the grip handle 12. A fastener 114 may secure the base 102 in the counterbore 35. At the other end of the grip handle 12, a fastener 116 may secure a sleeve 120 in the proximal counterbore 31. An internal screw thread 122 (FIG. 12) on the sleeve 120 may be located in the passage 41 that extends through the grip handle 12 along the axis 25. The shaft 14 may extend and may be movable axially through the passage 41, with the first screw thread 64 on the shaft 14 spaced radially inward from the internal screw thread 122 in the passage 41. The arms 90 on the ejector rod 86 may project outward through the slots 109 on the paddles 18 to slide along the slots 109 as the pusher block 20 moves axially with the shaft 14.

Axial movement of the shaft 14 and the pusher block 20 can be accomplished in either of two different modes of operation. In the first mode, the shaft 14 can slide freely through the passage 41 until the second screw thread 68 (adjacent to the T-handle 16) on the shaft 14 moves forward into engagement with the internal screw thread 122 in the sleeve 120 on the grip handle 12. Further advancement of the pusher block 20 and the implant 22 may be accomplished by rotating the T-handle 16 relative to the grip handle 12 so as to screw the shaft 14 forward along the axis 25. In the second mode of operation, the shaft 14 does not slide freely through the passage 41 in the grip handle 12, but can be moved axially forward only by rotating the T-handle 16 to screw the shaft 14 through the passage 41. The operator can shift the inserter 10 between the two different modes of operation by shifting a clutch mechanism 130 that is mounted on the grip handle 12.

Figure 14:
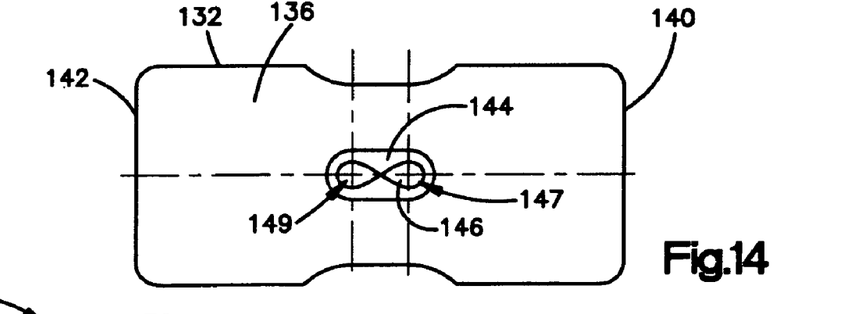
FIG. 14 is a top view of the part shown in FIG. 13.
Figures 15, 16, 17:
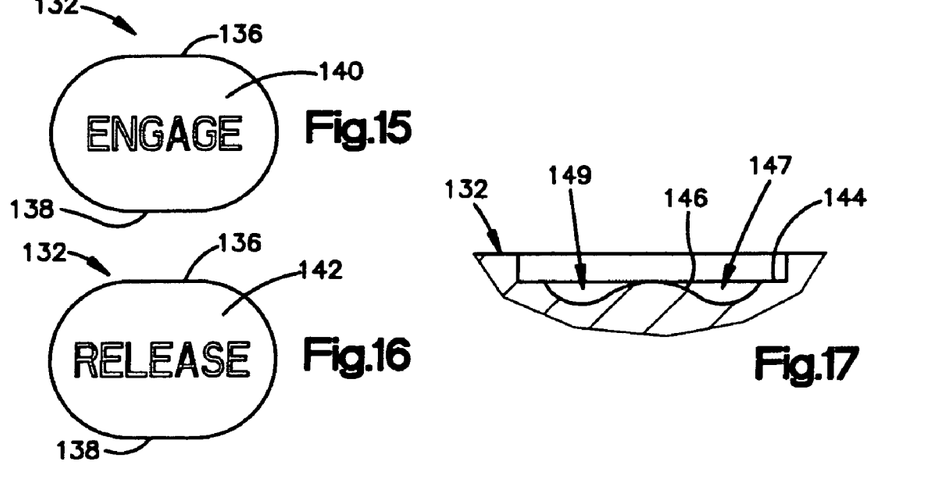
FIG. 15 is an end view taken on line 15-15 of FIG. 13.
FIG. 16 is an end view taken on line 16-16 of FIG. 13.
FIG. 17 is an enlarged partial view of the part shown in FIG. 13.
Figure 18:
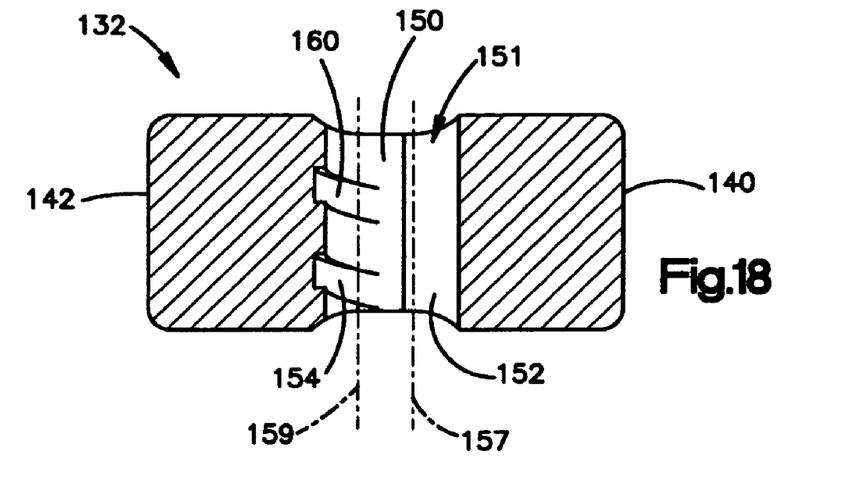
FIG. 18 is a sectional view taken on line 18-18 of FIG. 13.
Figure 19:
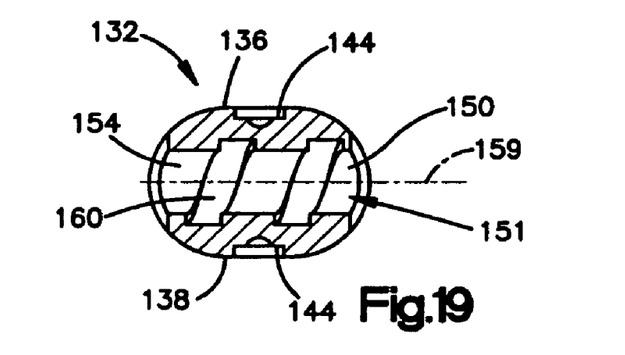
FIG. 19 is a sectional view taken on line 19-19 of FIG. 13.

The clutch mechanism 130 may include a moveable clutch member 132 and a pair of fasteners (e.g., ball detents 134) operably connected to the handle 12. As shown in FIGS. 13-19, the clutch member 132 may be a cylindrical part with flattened upper and lower side surfaces 136 and 138. End surfaces 140 and 142 of the clutch member 132 can have actuation indicia, as shown in FIGS. 15 and 16. A pair of recessed surfaces 144 may be located (e.g., centrally) on at least one opposite side surface 136 and 138. The recessed surfaces 144 may be alike, and each may have a cam surface portion 146 (FIG. 19) defining a pair of pockets 147 and 149. As best shown in FIG. 14, the pockets 147 and 149 in the illustrated example may have tear-drop shapes extending oppositely away from each other lengthwise of the clutch member 132.

An inner surface 150 of the clutch member 132 may define a passage 151. The inner surface 150 may have distinct portions 152 and 154 on opposite sides of the passage 151. The first side portion 152 of the inner surface 150 may have a semi-cylindrical contour centered on a first axis 157. The second side portion 154 may have a semi-cylindrical contour centered on a second axis 159 that is spaced from the first axis 157, and may define a screw thread 160 extending partly around the second axis 159.

Figure 20:
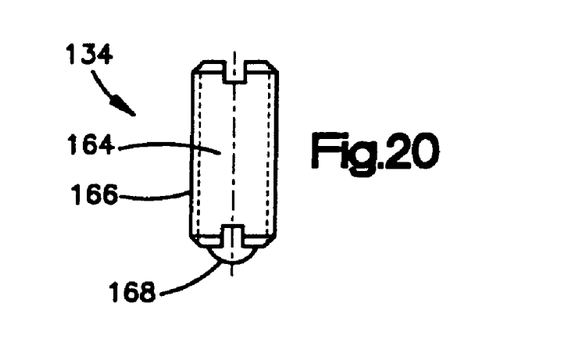
FIG. 20 is a side view of a part of the inserter of FIG. 1.

Referring again to FIGS. 10 and 11, the clutch member 132 may extend through the transverse passage 43 in the grip handle 12. The passage 151 that extends through the clutch member 132 may be aligned with the longitudinal passage 41 in the grip handle 12. The ball detents 134 may engage and may retain the clutch member 132 on the grip handle 12. Specifically, each ball detent 134 may have a casing 164 with an external screw thread 166, as shown in FIG. 20. The ball detents 134 may be screwed into the narrow bores 47 (FIG. 2) in the grip handle 12 to positions in which the balls 168 at the ends of the casings 164 project into the passage 43. When the clutch member 132 is installed in the passage 43, the balls 168 may both be seated in either the first or second pockets 147 or 149 in the clutch member 132. By pushing alternately against the two end surfaces 140 and 142, the operator can force the cam surfaces 146 to slide against the resistance of the ball detents 134 so as to shift the clutch member 132 back and forth between a first position in which the balls 168 are seated in the first pockets 147 and a second position in which the balls 168 are seated in the second pockets 149.

When the clutch member 132 is in the first position, the unthreaded inner surface 152 may be located beside the first screw thread 64 on the shaft 14, as shown in FIG. 11. The internal screw thread 160 at the opposite side of the passage 151 may then be spaced transversely from the first screw 64 thread on the shaft 14. Accordingly, the thread 160 does not mate with the thread 64, and the shaft 14 is free to slide along the axis 25.

When the clutch member 132 is shifted from the first position to the second position, the unthreaded inner surface 152 of the clutch member 132 is moved transversely away from the first screw thread 64 on the shaft 14. The internal screw thread 160 on the clutch member 132 may simultaneously be moved transversely into engagement with the first screw thread 64 on the shaft 14. Accordingly, when the clutch member 132 is in the second position, the operator can move the shaft 14 along the axis 25 only by rotating the T-handle 16 relative to the grip handle 12 so as to screw the shaft 14 through the passage 41 in the grip handle 12. The internal screw threads 160 and 122 may be respectively positioned, and have the same pitch, such that as the shaft 14 moves along the axis 25, the screw thread 64 on the shaft 14 mates simultaneously with the internal screw threads 160 and 122.

In use of the inserter 10, the operator may manually slide the implant 22 forward between the paddles 18 to spread them apart until their spring force holds the implant 22 in place. A rail-groove type relationship may be established between paddles 18 and the implant 22 to keep the implant 22 in proper alignment with the paddles 18 as the implant 22 is advanced distally. For example, each of the paddles 18 may have a plurality (e.g., two) rails 26 to engage corresponding groove(s) on the outer (e.g., upper and lower) surfaces of the implant 22.

The operator may move the shaft 14 and the pusher block 20 axially forward until the forward surface 82 of the pusher block 20 engages the complementary surface 84 of the implant 22. With the distal ends 24 of the paddles 18 inserted between a pair of vertebrae, and with the stop structures 110 abutting the vertebrae, further forward movement of the pusher block 20 forces the implant 22 between the distal ends 24 of the paddles 18. This moves the paddles 18 apart from each other to distract the vertebrae according to the thickness of the implant 22, and simultaneously moves the implant 22 into the intravertebral space. If the clutch member 132 is in the first position, the rod 14 and pusher block 20 may be advanced through this first range of movement merely by sliding the rod 14 forward along the axis 25 without the need to rotate the T-handle 16.

However, if the clutch member 132 is in the second position, the rod 14 and the pusher block 20 can be advanced through the first range of movement only by rotating the T-handle 16 to screw the rod 14 through the grip handle 12, as described above. In either case, a second range of movement follows as the second screw thread 68 on the shaft 14 moves axially into engagement with the internal screw thread 122 in the sleeve 120. As the shaft 14 is screwed forward through the second range of movement, the pusher block 20 drives the implant 22 out from between the distal ends 24 of the paddles 18. As the implant 22 moves beyond the distal ends 24 of the paddles 18 and in between adjacent vertebrae, the arms 90, 90a of the ejector rod 86, 86a may engage the outer walls of the adjacent vertebrae. Rotation of the shaft 14 may result in the arms 90, 90a pushing against the vertebrae, thereby causing the paddles 18 to be withdrawn from in between the vertebrae in the second range of movement. In the illustrated embodiments, the various ranges of threaded movement, effected by the various threaded regions, have the same respective pitches effecting the same rate or pace of movement along the respective regions.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. An apparatus for use in inserting a spinal implant between vertebrae, the apparatus comprising:
a handle structure having a longitudinal axis and a passage;
a shaft movable within the passage and at least a portion having a first screw thread;

a pusher block operably connected to the shaft and having a forward surface configured to contact the spinal implant;

a pair of paddles extending from the handle, the pair of paddles including a distal end positionable between the vertebrae, a proximal end attached to the handle, and a stop structure extending generally away from the longitudinal axis from at least one of the pair of paddles proximate the distal end, at least a portion of the shaft located between the pair of paddles, the paddles comprising separately flexible portions so that the distal ends are biased together, at least one of the pair of paddles has a slot therethrough extending generally parallel to the longitudinal axis, the at least one slot extending distally of the stop structure;

an ejector rod operatively connected to the pusher block, the ejector rod having at least one arm, the ejector rod, the pusher block and the shaft movable generally parallel to the longitudinal axis such that the at least one arm slides within the slot, the distal ends of the pair of paddles moving away from each other as the pusher block moves from the proximal end to the distal end; and a clutch member supported on the handle structure for movement into and out of engagement with the first screw thread.

2. The apparatus as defined in claim 1, wherein the handle structure has an internal screw thread, and the shaft has a second screw thread movable along the longitudinal axis into engagement with the internal screw thread on the handle structure when the clutch member is either engaged or disengaged with the first screw thread of the shaft.

3. The apparatus as defined in claim 1, wherein the pusher block has a circular bore therein to receive the ejector rod.

4. The apparatus as defined in claim 3, wherein the ejector rod comprises a central portion having a longitudinal axis and two arms extending from the central portion.

5. The apparatus as defined in claim 4, wherein the arms are offset from the longitudinal axis of the central portion.

6. The apparatus as defined in claim 4, wherein the central portion of the ejector rod comprises a plurality of indentations and a groove, the pusher block comprising at least one fastener for engaging the indentations and groove such that the ejector rod is rotatable relative to the pusher block.

7. The apparatus as defined in claim 1, wherein at least one of the pair of paddles has at least one ridge at the distal end thereof, the at least one ridge acting as a retention feature to prevent the apparatus from dislodging during operation.

8. The apparatus as defined in claim 1, wherein the clutch member comprises an opening therethrough having a first portion and a second portion.

9. The apparatus as defined in claim 8, wherein the first portion comprises a threaded portion and the second portion comprises an unthreaded portion.

10. The apparatus as defined in claim 1, wherein the paddles are configured as elongated leaf springs.

11. The apparatus as defined in claim 1, wherein at least one of the paddles includes at least one ridge at the distal end thereof, the at least one ridge acting as a retention feature to prevent the apparatus from dislodging during operation.

12. The apparatus of claim 11, wherein at least one of the paddles includes a pair of parallel ridges spaced apart from each other.

13. The apparatus of claim 11, wherein the at least one ridge is located distally of the stop structure.

14. The apparatus as defined in claim 1, wherein at least one of the paddles includes a rail extending from an inner surface thereof, the rail being sized and configured to engage a groove formed on an outer surface of the implant to keep the implant in alignment with the paddles as the implant is advanced distally during operation.

15. The apparatus as defined in claim 14, wherein at least one of the paddles comprises an opening such that when the ejector rod is positioned in the opening, the ejector rod is disengageable from the pusher block.

16. The apparatus as defined in claim 14, wherein at least one of the paddles comprises an opening such that when the ejector rod is positioned in the opening, the ejector rod is rotatable with respect to the pusher block.

17. The apparatus of claim 14, wherein each paddle includes a rail extending from an inner surface thereof, respectively.

18. The apparatus of claim 1 wherein the paddles are comprised of separately flexible portions of a unitary spring structure.

19. The apparatus of claim 1 wherein the at least one arm of the ejector rod is comprised of a first arm and a second arm, the slot in the at least one of the pair of paddles is comprised of a first slot in a first paddle of the pair of paddles and a second slot in a second paddle of the pair of paddles, the first arm extending through the first slot and the second arm extending through the second slot in an assembled configuration.

20. The apparatus of claim 1, wherein each paddle includes at least one ridge at the distal end thereof, the ridges acting as a retention feature to prevent the apparatus from dislodging during operation.

21. The apparatus of claim 1, wherein the forward surface of the pusher block is sized and configured to engage the spinal implant to prevent movement of the implant with respect to the paddles in one to three degrees of freedom.

22. An apparatus for use in inserting a spinal implant between vertebrae, the apparatus comprising:

a handle structure having a longitudinal axis and a passage;

a shaft movable within the passage and at least a portion having a first screw thread;

a pusher block operably connected to the shaft and having a forward surface configured to contact the spinal implant;

a pair of paddles extending from the handle, the pair of paddles including a distal end positionable between the vertebrae, a proximal end attached to the handle, and a stop structure extending generally away from the longitudinal axis from at least one of the pair of paddles proximate the distal end, at least a portion of the shaft located between the pair of paddles, the paddles comprising separately flexible portions so that the distal ends are biased together, at least one of the pair of paddles has a slot therethrough extending generally parallel to the longitudinal axis, the at least one slot extending distally of the stop structure;

an ejector rod operatively connected to the pusher block, the ejector rod having at least one arm, the ejector rod, the pusher block and the shaft movable generally parallel to the longitudinal axis such that the at least one arm slides within the slot, the distal ends of the pair of paddles moving away from each other as the pusher block moves from the proximal end to the distal end; and a clutch member supported on the handle structure for movement into and out of engagement with the first screw thread, the clutch member including an opening therethrough having a first portion and a second portion, the clutch member further comprises a first side portion and at least a pair of pockets on the side portion, the handle having a first fastener for selectively engaging only one of the pair of pockets at a time.

23. The apparatus as defined in claim 22, wherein the clutch member further comprises a second side portion and a second pair of pockets on the second side portion, the handle having a second fastener for selectively engaging only one of the second pair of pockets at a time.

24. The apparatus as defined in claim 23, wherein the first and second fasteners are ball detents positioned through the handle.

25. An apparatus having a longitudinal axis for inserting a spinal implant between vertebrae, the apparatus comprising:
- a handle structure having a passage therethrough;
- a shaft moveable within the passage;
- a pair of flexible paddles having a proximal end and a distal end, the proximal end of the paddles connected to the handle structure and a stop structure extending generally away from the longitudinal axis from each of the pair of paddles proximate the distal end, the paddles being configured so that they converge at the distal ends so that the distal end are biased together to secure the implant between the pair of flexible paddles, wherein at least one of the pair of paddles has a slot therethrough extending generally parallel to the longitudinal axis;
- a pusher block associated with the shaft and positioned between the pair of paddles, the pusher block having a forward surface configured to engage the spinal implant; and
- an ejector rod having at least one arm, wherein the ejector rod is mounted to the pusher block, the ejector rod, pusher block and shaft movable generally parallel to the longitudinal axis such that the at least one arm slides along the slot, the distal ends of the pair of paddles moving away from each other as the pusher block moves from the proximal end to the distal end;
- wherein the shaft includes a first screw thread and a second screw thread, the first screw thread selectively engageable with internal screw threads on a clutch member that is movably mounted to the handle structure, the second screw thread selectively engageable with an internal screw thread in a sleeve that is mounted to the handle structure.

26. An apparatus having a longitudinal axis for inserting a spinal implant between vertebrae, the apparatus comprising:
- a handle structure having a passage therethrough;
- a shaft moveable within the passage;
- a pair of flexible paddles having a proximal end and a distal end, the proximal end of the paddles connected to the handle structure and a stop structure extending generally away from the longitudinal axis from each of the pair of paddles proximate the distal end, the paddles being configured so that they converge at the distal ends so that the distal end are biased together to secure the implant between the pair of flexible paddles, wherein at least one of the pair of paddles has a slot therethrough extending generally parallel to the longitudinal axis;
- a pusher block associated with the shaft and positioned between the pair of paddles, the pusher block having a forward surface configured to engage the spinal implant;
- an ejector rod having at least one arm, wherein the ejector rod is mounted to the pusher block, the ejector rod, pusher block and shaft movable generally parallel to the longitudinal axis such that the at least one arm slides along the slot, the distal ends of the pair of paddles moving away from each other as the pusher block moves from the proximal end to the distal end; and
- a clutch member having at least a portion with screw threads, wherein the clutch member is supported on the handle for movement into and out of engagement with a first screw thread on the shaft such that the shaft only rotates through a first range of movement in the passage when the clutch member is engaged with the first screw thread.

* * * * *